United States Patent
Brooks

(10) Patent No.: US 10,512,655 B1
(45) Date of Patent: Dec. 24, 2019

(54) METHODS AND COMPOSITIONS FOR THE TOPICAL TREATMENT OF PERIPHERAL NEUROPATHY

(71) Applicant: Jeffrey S. Brooks, Inc., St. Louis, MO (US)

(72) Inventor: Jeffrey S. Brooks, St. Louis, MO (US)

(73) Assignee: Jeffrey S. Brooks, Inc., St. Louis, MO (US)

( * ) Notice: Subject to any disclaimer, the term of this patent is extended or adjusted under 35 U.S.C. 154(b) by 296 days.

(21) Appl. No.: 14/202,161

(22) Filed: Mar. 10, 2014

Related U.S. Application Data

(60) Provisional application No. 61/777,582, filed on Mar. 12, 2013.

(51) Int. Cl.
| | | |
|---|---|---|
| *A61K 31/675* | (2006.01) | |
| *A61K 45/06* | (2006.01) | |
| *A61K 31/485* | (2006.01) | |
| *A61K 31/519* | (2006.01) | |

(52) U.S. Cl.
CPC .......... *A61K 31/675* (2013.01); *A61K 31/485* (2013.01); *A61K 31/519* (2013.01); *A61K 45/06* (2013.01)

(58) Field of Classification Search
CPC .............................. A61K 31/675; A61K 31/51
See application file for complete search history.

(56) References Cited

U.S. PATENT DOCUMENTS

| | | | | |
|---|---|---|---|---|
| 6,143,278 | A | 11/2000 | Elkhoury | |
| 7,235,249 | B2 | 6/2007 | Bissett | |
| 7,666,442 | B2 | 2/2010 | Morariu | |
| 8,137,711 | B2 | 3/2012 | Wolicki | |
| 2005/0019354 | A1 | 1/2005 | Perricone | |
| 2006/0045896 | A1* | 3/2006 | Morariu | A61K 8/4926 424/401 |
| 2006/0084066 | A1 | 4/2006 | Sah et al. | |
| 2007/0190126 | A1* | 8/2007 | Stuart | A61K 9/0014 424/449 |
| 2008/0102137 | A1 | 5/2008 | Guffey | |
| 2009/0311167 | A1 | 12/2009 | Height et al. | |
| 2010/0210582 | A1 | 8/2010 | Stewart et al. | |
| 2010/0279984 | A1 | 11/2010 | Bonke et al. | |
| 2011/0263710 | A1 | 10/2011 | Moskowitz et al. | |

OTHER PUBLICATIONS

Smith et al., Percutaneous Penetration Enhancers, Chapter 1.1 and Chapter 1.2, 1995, pp. 1-20.
Ghosh et al., "Methods of Enhancement of Transdermal Drug Delivery: Part I, Physical and Biochemical approaches", Pharmaceutical Technology, 17(3), 72-98, Mar. 1993.
Ghosh et al., "Methods of Enhancement of Transdermal Drug Delivery: Part IIA, Chemical Permeation Enhancers", Pharmaceutical Technology, 17(4), 62-90, Apr. 1993.
Ghosh et al., "Methods of Enhancement of Transdermal Drug Delivery: Part IIB, Chemical Permeation Enhancers", Pharmaceutical Technology, 17(5), 68-76, May 1993.
Swinyard et al., "Pharmaceutical Necessities", Remington's Pharmaceutical Sciences, 1985, 17th Edition, Chapter 68, pp. 1278-1320.
Head, K., "Peripheral Neuropathy: Pathogenic Mechanisms and Alternative Therapies", Alternative Medicine Review, 2006, 11(4): 294-329.
Balakumar, P. et al., "The multifaceted therapeutic potential of benfotiamine", Pharmacological Research, 2010, 61: 482-488.
Fraser, D.A. et al., "The effects of long-term oral benfotiamine supplementation on peripheral nerve function and inflammatory markers in patients with type 1 diabetes: a 24-month, double-blind, randomized, placebo-controlled trial", Diabetes Care, 2012, 35(5):1095-1097.
Fonseca et al., "Metanx in Type 2 Diabetes with Peripheral Neuropathy: A Randomized Trial", A Med J, 2013, 126(2): 141-149.
Bighley et al., "Salt Forms of Drugs and Absorption," in Encyclopedia of Pharmaceutical Technology, J. Swarbrick and J.C. Boylan, Eds. (Marcel Dekker, New York, 1996), vol. 13, pp. 453-499.
Hahn, John, "The Naturopathic Management of Diabetic Peripheral Neuropathy", Townsend Letter, 2010, Feb.-March, pp. 56-62.
Parminder et al., "Current Therapeutic Strategies in Diabetic Neuropathy", International Research Journal of Pharmacy, 2012, 3(3): 22-29.
Boulton et al., "Diabetic Peripheral Neuropathy: Diagnosis and Management", Medscape Education, pp. 1-49, released Aug. 16, 2011.
St. Onge et al., "Pain Associated with Diabetic Peripheral Neuropathy", P&T, Mar. 2008, 33(3): 166-176.
Ang et al., "Vitamin B for treating peripheral neuropathy (Review)", Cochrane Database System Review, 2008, 16(3): 1-39.
Cheng et al., "Painful Diabetic Neuropathy", Neuropathic Pain: Mechanisms, Diagnosis and Treatment, Chapter 11, 2012, pp. 165-189.
"Topical Drugs", Remington: The Science and Practice of Pharmacy, 20th edition, (Lippincott, Williams & Wilkins, 2003), Chapter 65, pp. 1200-1218.
Authia Cream, Commercial product description [online], Westlake Laboratories Inc. [retrieved on Aug. 15, 2014]. Retrieved from the Internet: <URL: www.westlake-labs.com/products/authia-cream>.
Neuro-Immune Stabilizer Topical Cream, Commercial product description [online], Neuro Biologix [retrieved on Aug. 15, 2014]. Retrieved from the Internet: <URL: www.neurobiologix.com/Neuro-Immune-Stabilizer-B12-136-Vitamin-D-Cream-p/46.htm>.
Topical B Complex, Commercial product description [online], Sarati Labs [retrieved on Aug. 15, 2014], Retrieved from the Internet: <URL: www.amazon.com/Topical-Complex-Sarati-Labs-Tube/dp/B000NGM342>.

(Continued)

*Primary Examiner* — Rachael E Bredefeld

(74) *Attorney, Agent, or Firm* — Stinson LLP

(57) ABSTRACT

Methods for the treatment of peripheral neuropathy are provided which include applying a topical composition to a peripheral appendage of a subject in need of such treatment. The topical composition includes a B1 vitamer, a B6 vitamer, and a B9 vitamer in a dermatologically acceptable carrier. The methods are effective in preventing further degeneration and/or restoring epidermal nerve fiber density (ENFD) in patients with peripheral neuropathy, and in preventing or alleviating neuropathic pain.

29 Claims, No Drawings

(56) References Cited

OTHER PUBLICATIONS

Jayabalan, B., et al., "Vitamin B Supplementation for Diabetic Peripheral Neuropathy," Singapore Medical Journal, 2016, pp. 55-59, vol. 57, No. 2.

* cited by examiner

METHODS AND COMPOSITIONS FOR THE TOPICAL TREATMENT OF PERIPHERAL NEUROPATHY

CROSS-REFERENCE TO RELATED APPLICATIONS

This application claims the benefit of U.S. Provisional Patent Application Ser. No. 61/777,582, filed Mar. 12, 2013, the entirety of which is herein incorporated by reference.

FIELD OF THE INVENTION

The present invention relates to methods and compositions for the topical treatment of peripheral neuropathy. More particularly, the present invention relates to methods and topical compositions to decrease neuropathic pain and increase epidermal nerve fiber density.

BACKGROUND OF THE INVENTION

Peripheral neuropathy, characterized by slow nerve conduction and by pain, numbness, and tingling in the extremities, can be extremely debilitating. Pain is a serious symptom for many patients, and may be described as a dull aching sensation, an intense burning sensation, or as intermittent, stabbing pain. On occasion, patients notice that their skin is hypersensitive to tactile sensation, such as from standing on their feet or from the touch of clothing or bedding. Some patients note an exaggerated pain resulting from stimulus to the affected area, a form of pain termed allodynia.

Peripheral neuropathy encompasses a wide spectrum of clinical disorders that affect sensory, motor, and autonomic peripheral nerve fibers. Nerve fiber dysfunction can be the result of genetics, systemic or infectious disease, environmental toxins, alcoholism, nutritional deficiencies, or the side effect of certain medications. Peripheral neuropathy can also be caused by traumatic injury, surgery, radiation, and chemotherapy.

Diabetic peripheral neuropathy (DPN) is one of the most common complications of diabetes, affecting about half of all people with diabetes at some point in their life. The cause of DPN is still under debate, and this lack of knowledge prevents the development of mechanism specific therapies. DPN can also manifest in pre-diabetic individuals with abnormal glucose tolerance. It is known that nerve fiber regeneration is impaired in diabetic nerve, and contributes to the relentless nerve fiber loss characterizing this disorder.

The symptoms of diabetic peripheral neuropathy may include pain, loss of sensory perception, weakness, unsteadiness, and ataxia. Constant pain, which affects 16-26% of people with diabetes, can lead to other health issues such as fatigue, depression, insomnia, and anxiety. Further, lack of protective sensation of the feet puts patients with DPN at high risk for foot ulcerations and non-traumatic amputations resulting from undetected injury.

Pharmacologic management of DPN includes two approaches: (1) treatments that slow the progression of neuropathy and (2) treatments that provide symptom relief. No treatments have yet been identified that can reverse nerve cell damage or loss. The optimization of glycemic control through diet and pharmacotherapy can delay the progression of diabetic neuropathy. Other lifestyle modifications include exercise, weight reduction, smoking cessation, and avoidance of excess alcohol consumption. Neuropathic pain typically does not respond to simple analgesics, and its potential chronicity precludes narcotic therapy as a first choice because of issues associated with tolerance and addiction. Drug therapy for symptomatic relief in DPN includes the use of tricyclic antidepressants, serotonin and norepinephrine reuptake inhibitors, N-methyl-D-aspartate (NMDA) antagonists, anticonvulsants, and opioids. Unfortunately, there is no evidence that any of these agents modifies the underlying pathophysiology of DPN.

To date, three oral medications have been approved by the U.S. Food and Drug Administration (FDA) for treatment of DPN pain. Pregabalin (Lyrica®, commercially available from Pfizer, New York, N.Y.) is an anticonvulsant agent that binds with high affinity to the α2-δ subunit of calcium channels. This is thought to produce an analgesic effect by decreasing $Ca^{+2}$ influx into nerve terminals and decreases neurotransmitter release. Side effects of pregabalin include dizziness, somnolence, dry mouth, edema, blurred vision, weight gain, and attention deficit. A further side effect associated with Lyrica® is an increased risk of suicidal thoughts and behavior.

Duloxetine (Cymbalta®, commercially available from Eli Lilly, Indianapolis, Ind.) is an antidepressant that inhibits serotonin and norepinephrine reuptake. Its mechanism of action involves an increased availability of 5-hydroxytryptamine and noradrenaline, which suppress pain impulses. Side effects of duloxetine include headache, fatigue, nauseas, constipation, and increased blood pressure. This drug cannot be used to treat patients with liver disease, renal failure, or glaucoma.

Tramadol (Nucynta®, commercially available from Johnson & Johnson, New Brunswick, N.J.) is a µ-opioid agonist that also inhibits reuptake of serotonin. Adverse effects include respiratory depression, nausea, somnolence, vomiting, and headache. Patients receiving tramadol require careful monitoring for signs of abuse and addiction. Risk for addiction occurs even under appropriate medical use, and is increased for patients with a family history of substance abuse (including alcohol or drugs) or mental illness (e.g. major depression).

Several topical agents (creams, gels, solutions, sprays, ointments, and patches) have been utilized for the relief of peripheral neuropathic pain including capsaicin, isosorbide dinitrate, nitroglycerin, and lidocaine. Most provide only temporary relief to subjects suffering from neuropathic pain. At present, none of these treatments has demonstrated sufficient efficacy in controlled clinical trials to warrant approval for the treatment of neuropathic pain by the FDA. For example, U.S. Pat. No. 6,143,278 is directed to methods and pharmaceutical compositions for the topical administration of opioid analgesic drugs without substantial transdermal or transmucosal migration of opioid agent into the systemic circulation. However, patients suffering from DPN experienced no pain relief when treated with topical morphine in a KY gel non-occlusive vehicle. U.S. Pat. No. 8,137,711 discloses a topical composition for the treatment of neuropathic pain comprising three active ingredients (ketamine, gabapentin, and clonidine) within a transdermal base reported to synergistically or comprehensively affect multiple pathways and provide a "synergistic shotgun effect." Side effects are possible, especially dizziness or drowsiness. Manifestation of side effects is a limiting factor for dosing and frequency of application of the topical composition, as well as the site of application and the time of application.

Non-pharmacological treatments of peripheral neuropathy are often categorized as alternative therapies (Head, K., Alternative Medicine Review, 2006, 11(4): 294-329, "Peripheral Neuropathy: Pathogenic Mechanisms and Alternative Therapies"). These treatments include the use of acupuncture, magnet therapy, yoga, mineral supplements (zinc, magnesium, chromium), and various nutrient/botanical therapies (alpha-lipoic acid, acetyl-L-carnitine, thiamine/benfotiamine, methylcobalamin, vitamin E, glutathione, folate, pyridoxine, biotin, myoinositol, omega-3- and omega-6-fatty acids, L-arginine, L-glutamine, taurine, N-acetylcysteine, and St. John's wort). Alternative therapies are typically without side effect and address nutrient deficiencies, oxidative stress, and other etiological factors associated with the development of peripheral neuropathy.

Benfotiamine, a synthetic S-acyl derivative of thiamine, has been reported to prevent the progression of many serious complications of prolonged hyperglycemia, and to have therapeutic applications in diabetic patients. The effects attributed to benfotiamine were extrapolated from in vitro and animal studies (Balakumar, P. et al., *The multifaceted therapeutic potential of benfotiamine*, PHARMACOLOGICAL RESEARCH, 2010, 61: 482-488). However, the results of a recent clinical trial. concluded that high-dose benfotiamine (300 mg/day) oral supplementation over 24 months has no significant effects upon peripheral nerve function or soluble markers of inflammation in patients with type 1 diabetes, and a trend toward deterioration (Fraser, D. A. et al., *The effects of long-term oral benfotiamine supplementation on peripheral nerve function and inflammatory markers in patients with type 1 diabetes: a 24-month, double-blind, randomized, placebo-controlled trial*, DIABETES CARE, 2012, 35(5):1095-1097).

Various combinations of B vitamins have also been evaluated for the oral treatment of DPN. Metanx®, for example, is a prescription medical food for the dietary management of endothelial dysfunction in patients with diabetic peripheral neuropathy. Metanx® oral tablets comprise the active ingredients calcium L-methylfolate (LMF), pyridoxal-5'-phosphate, and methylcobalamin. Recent clinical trials support the use of Metanx® as a safe approach for short-term alleviation of symptoms associated with diabetic peripheral neuropathy. However, its impact on long-term outcomes is not known (Fonseca, Vivian A. et al., *Metanx in Type 2 Diabetes with Peripheral Neuropathy: A Randomized Trial*, A MED J, 2013, 126(2): 141-149).

While conventional medicine can offer some relief from neuropathic pain, the potential side effects or addictive nature of many of the medications render long-term use undesirable. Further, pain medications primarily mask symptoms and do not address the underlying pathologies.

SUMMARY OF THE INVENTION

One aspect of the invention is directed to a topical composition comprising about 5.0 to 25.0 wt. % of a B1 vitamer, about 0.1 to 15.0 wt. % of a B6 vitamer, and about 0.01 to 5.0 wt. % of a B9 vitamer in a dermatologically acceptable carrier. The topical composition can further include about 0.001 to 0.5 wt. % of an opioid analgesic agent, about 0.001 to 0.5 wt. % of a calcium channel alpha-two-delta ($\alpha_2\delta$) ligand, or about 0.001 to 0.05 wt. % of a voltage-gated sodium channel (VGSC) blocker, from about 0.001 to 10 wt. % of at least one vitamin, fatty acid, antioxidant, anti-inflammatory agent, antifungal agent, antimicrobial agent, moisturizing agent, emollient, exfoliant, or carbamide. The dermatologically acceptable carrier can include an ointment base, and the dermatologically acceptable carrier can be at least 70 wt. % of the topical composition. The topical composition can be in the form of a cream, lotion, serum, oil, ointment, gel, paste, liniment, powder, spray, aerosol, roll-on liquid, or foam, or can be impregnated into, or used as a coating on, a bandage, patch, adhesive material, dressing, support wrap, glove, sock, footwear, or fabric.

The topical composition can be a nutritional supplement or a food. Without being bound by any particular theory, it is believed that the supplement or food provides nutrition to the skin to support healthy skin function.

Another aspect of the invention is directed to a method for the treatment of peripheral neuropathy comprising applying to a peripheral appendage of a subject in need of such treatment the topical composition as described above. The topical composition can be applied at least twice daily, such as application three to four times daily for about the first month of use, followed by application twice daily thereafter. The method can further comprise applying a topical moisturizer to the appendage at least 20 minutes after application of the topical composition, such as 20 to 30 minutes after application of the topical composition. The method can comprise exfoliating the appendage at least one hour after application of the topical composition, such as by mechanical exfoliating or by chemically exfoliating via application of an exfoliating composition to the appendage. The method can relieve pain. The method can also increase epidermal nerve fiber density after six months of treatment as compared to the epidermal nerve fiber density of the subject when treatment is initiated. The peripheral neuropathy can be induced by alcohol, a therapeutic drug, or a toxic agent, result from a systemic or infectious disease, induced by chemotherapy, radiation therapy, surgery, or traumatic injury, genetically acquired, or can be nutritional polyneuropathy, diabetic peripheral neuropathy, alcoholic peripheral neuropathy, or nutritional polyneuropathy. The subject can be a human, and can be a subject who has a peripheral neuropathy or who is at risk of having a peripheral neuropathy. The appendage can comprise a hand, a foot, or a limb stump.

A further aspect of the invention is a method for the treatment of pain and other symptoms associated with peripheral neuropathy in a subject in need of such treatment, comprising applying the topical composition as described above to an appendage of the subject.

A still further aspect of the invention is a method for increasing epidermal nerve fiber density in the skin of a subject who has a peripheral neuropathy or is at risk of having a peripheral neuropathy (such as diabetic peripheral neuropathy in a diabetic or pre-diabetic subject), comprising applying the topical composition as described above to an appendage of the subject.

Other objects and features will be in part apparent and in part pointed out hereinafter.

DESCRIPTION OF THE PREFERRED EMBODIMENTS

The methods of the present invention comprise the application of a topical composition comprising a B1 vitamer, a B6 vitamer, and a B9 vitamer to treat peripheral neuropathy. The topical compositions are effective in preventing further degeneration and/or restoring epidermal nerve fiber density (ENFD) in patients with peripheral neuropathy, and in preventing or alleviating neuropathic pain, and have no adverse side effects.

The topical compositions of the present invention comprise a therapeutically effective amount of a B1 vitamer, a B6 vitamer, and a B9 vitamer in a dermatologically acceptable carrier. Preferably, the composition comprises at least a B1 vitamer, a B6 vitamer, or a B9 vitamer in an amount sufficient to both decrease neuropathic pain (if present) and increase epidermal nerve fiber density (ENFD).

The active ingredients typically do not exceed 40 wt. % of the topical composition, in which case the carrier and any optional inactive ingredients comprise at least 60 wt. % of the topical composition. Preferably, the active ingredients comprise up to 30 wt. % of the topical composition. The carrier and any optional inactive ingredients comprise at least 70 wt. % of the topical composition.

In a method of treatment of peripheral neuropathy according to the present invention, a topical composition as described herein is applied to a peripheral appendage of a subject in need thereof. The topical composition can be applied to the skin at the site of an actual peripheral neuropathy, or to the skin at a site where there is risk of a peripheral neuropathy. For example, the topical composition may be applied by spreading a layer of cream on the skin at the affected site. The topical composition may be gently rubbed into the skin and/or allowed to be absorbed by the skin. Application of the topical composition may be self-performed by the patient.

The compositions are applied to a peripheral appendage, such as hands, feet, or limb stumps, of a subject in need of such treatment. Typically, the composition is applied topically to an entire appendage, to all appendages, or to a portion of an appendage where pain, tingling, or other symptomology has occurred or is occurring.

The topical composition is preferably applied to clean skin. Washing the appendages prior to application of the topical composition is recommended.

Typically, a suitable amount of the topical composition described herein is applied one to four times daily. Preferably, the composition is applied two to four times daily. Preferably, when any additional application is recommended in the beginning of treatment, the additional application of topical composition occurs at least one hour after the prior application of topical composition. Treatment may be continued indefinitely to relieve pain. A reduced number of applications may be recommended to prevent the return of symptoms as directed by a physician once epidermal nerve fiber density has been restored or improved and symptoms have been relieved. A subject typically experiences an improvement of their peripheral neuropathy within six months of treatment. The period of time in which improvement of the subject's condition is observed may depend on the severity of the subject's condition and the subject's neurologic status.

The amount of topical composition used and the frequency of application may decrease over time. For example, the topical composition may be applied 3 to 4 times per day for the initial month of use, and then applied twice daily thereafter. No significant adverse effects have been observed upon prolonged use of the topical composition.

If the topical composition includes an opioid or analgesic, then a suitable amount of the topical composition described herein is applied one to four times daily as needed to relief pain. Preferably, the composition is applied two to four times daily to relief pain.

The skin which has been treated with the topical composition of the invention can be further treated with a moisturizer. Preferably, a topical moisturizer is applied at least 20 minutes, such as 20 to 30 minutes, after the application of the topical composition.

The skin to which the topical composition has been applied, with or without subsequent application of moisturizer, can be exfoliated either mechanically or chemically. Preferably, the subject exfoliates the appendage before bedtime at least one hour after application of the topical composition; the exfoliant can remain on the appendage throughout the night. Exfoliation of excessively dry skin with cracking can be accomplished by mechanical means, for example, with a scrub, microfiber cloth, bath sponge, pumice stone, file, microbeads, loofah, brush, or microdermabrasion. A chemical exfoliant can be applied following mechanical exfoliation.

A preferred method of treating peripheral neuropathy comprises washing a peripheral appendage; applying the topical composition to the appendage after washing; optionally applying a topical moisturizer to the appendage about 20 to 30 minutes after applying the topical composition; washing the appendage about 6 to 12 hours after the first application of the topical composition; applying the topical composition to the appendage after the second washing of the appendage; and optionally exfoliating the skin of the appendage at least one hour after the second application of the topical composition.

The most preferred method of treating peripheral neuropathy comprises washing a peripheral appendage in the morning; applying the topical composition to the appendage in the morning after washing; applying a topical moisturizer to the appendage about 20 to 30 minutes after applying the topical composition; washing the appendage in the evening; applying the topical composition to the appendage after the second washing; and exfoliating the skin of the appendage at least one hour after the second application of the topical composition. If a chemical exfoliant is applied to the appendage, it can remain on the skin through the night.

The peripheral neuropathy can be induced by alcohol, a therapeutic drug, or a toxic agent, result from a systemic or infectious disease, induced by chemotherapy, radiation therapy, surgery, or traumatic injury, genetically acquired, or can be nutritional polyneuropathy, diabetic peripheral neuropathy, alcoholic peripheral neuropathy, or nutritional polyneuropathy. For example, the peripheral neuropathy can be alcohol induced neuropathy, neuropathy resulting from an amputation, or phantom limb pain.

A subject can be evaluated by a podiatrist, neurologist, pain management physician, a physician, or other health care worker (i.e. medical nurse practitioner) to determine the need for treatment for peripheral neuropathy. Initially, the subject may be evaluated with a screening test which assesses the appearance of the skin and elasticity, peripheral appendage strength and flexibility, gait, presence of ulceration, and ankle reflexes, and Semmes Weinstein filament testing may be performed. The screening test can be followed by electromyography to evaluate electrical potential generated by muscle cells in the peripheral appendage, ultrasound therapy and/or blood testing.

The subject can be an animal such as a mammal. Preferably, the subject in need of treatment is a human.

The efficacy of the methods of the invention and of the topical composition in increasing epidermal nerve fiber density can be evaluated with a skin punch biopsy to remove a 3 mm tissue specimen of the epidermis, dermis and subcutaneous fat from the appendage being treated. The tissue specimen is analyzed with an electronic microscope to determine the number of epidermal nerve fibers in a length of the tissue. Normal epidermis has 7.1 fibers per millimeter of the tissue specimen. A subject typically experiences symptomatology when the epidermis has about 3 fibers over the 3 mm length of the tissue specimen. The topical composition and methods of the invention are effective in some subjects in restoring abnormal epidermis to normal such that, for example, a subject with an ENFD of 3 fibers is returned to 6 or 7 fibers in a punch biopsy tissue sample after several months of treatment.

While not being bound by theory, it is believed that as a result of topical administration to the skin, the exogenously added active ingredients tend to concentrate in the local areas, where they overwhelm the pain-inducing effect of inflammation or nerve injury on the excitatory nerves, reducing the electrical signals of the local nerves. Thus, local relief from the source of pain at the local site is obtained without ever increasing substantially the concentration of the active ingredients in the bloodstream or the brain. As a result, the patient obtains pain relief without the unfortunate side effects usually encountered with conventional pain medications. It is also believed that the methods of the invention increase the amount of nitrous oxide at the site of local administration, resulting in increased blood flow to the skin due to the vasodilatory effect of nitrous oxide, and nerve regeneration.

The methods of the invention can also include a determination of patient compliance. For example, a skin biopsy sample can be obtained from the appendage both before and after a period of treatment with the topical composition. An amount of at least one nucleic acid or protein in the sample, which is a surrogate marker of peripheral neuropathy and/or neuropathic pain, can be determined by conventional methods for analysis of gene expression. The change in the amount of the nucleic acid or protein present after the treatment period as compared to the amount present before treatment can indicate the subject's compliance with the treatment protocol. Preferably, the skin biopsy sample is a skin punch biopsy sample, and compliance is determined after the subject indicates that symptomology of peripheral neuropathy has been alleviated. One such method for determining such a change in a surrogate marker of peripheral neuropathy or neuropathic pain is described in US 2006/0084066A1, which is incorporated by reference herein its methods of identifying such surrogate markers and for the surrogate markers described therein.

In considering the components of the topical compositions of the invention, B vitamers include, but are not limited to, thiamine, thiamine monophosphate, thiamine diphosphate (also known as thiamine pyrophosphate), thiamine triphosphate, benfotiamine, or a pharmaceutically acceptable salt thereof. The amount of B1 vitamer in the topical composition ranges from about 5.0 to about 25.0 wt. %, preferably about 10 to about 25.0 wt. %, and most preferably about 10.0 to about 20.0 wt. %. Benfotiamine is a preferred B1 vitamer.

B6 vitamers, include, but are not limited to, pyridoxine (PN, also called pyridoxal), pyridoxal (PL), pyridoxamine (PM), or pharmaceutically acceptable salt or a 5'-phosphorylated derivative thereof (i.e., pyridoxine-5'-phosphate, pyridoxal-5'-phosphate, or pyridoxamine. -5'-phosphate). B6 vitamers that are prodrugs include, for example, an acetate ester or other ester of any of the available hydroxyl groups of PN, PL or PM, since the esters are likely to be hydrolyzed by specific or non-specific esterases. The amount of B6 vitamer in the topical composition ranges from about 0.1 to about 15.0 wt. %, preferably about 0.5 to about 10.0 wt. %, and most preferably from about 1.0 to about 5.0 wt. %. Pyridoxal-5'-phosphate (PLP) is a preferred B6 vitamer.

B9 vitamers, include, but are not limited to, folic acid, dihydrofolate, tetrahydrofolate, 5,10-methylenetetrahydrofolate, 5-formiminotetrahydofolate, 5-formyltetrahydrofolate (folinic acid), 5-methyltetrahydrofolate (levomefolic acid), or pharmaceutically acceptable salt or a glutamyl derivative thereof. The amount of B9 vitamer in the topical composition ranges from about 0.01 to about 5.0 wt. %, preferably about 0.05 to about 2.0 wt. %, and most preferably from about 0.1 to about 1.0 wt. %. The preferred B9 vitamer is calcium 5-methyltetrahydrofolate (5-MTHF $Ca^{2+}$).

A salt of the B1 vitamer, B6 vitamer or B9 vitamer can be any pharmaceutically acceptable salt. Pharmaceutically acceptable salts include salts of acidic or basic groups. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, and p-toluenesulfonate salts. Suitable base salts include, but are not limited to, aluminum, calcium, lithium, magnesium, potassium, sodium, zinc, and diethanolamine salts. Suitable pharmaceutically acceptable salts are described in Berge et al., *Salt Forms of Drugs and Absorption*, in 13 ENCYCLOPEDIA OF PHARMACEUTICAL TECHNOLOGY 453-499 (J. Swarbrick & J Boylan ed., 1996), which is incorporated herein by reference.

The topical compositions may further comprise an additional analgesic agent. The analgesic agent may be an opioid analgesic such as, for example, morphine, hydromorphone, oxycodone, hydrocodone, oxymorphone, codeine, tramadol, tapentadol, buprenorphine, norbuprenorphine, fentanyl, levorphanol, methadone, loperamide, or a pharmaceutically acceptable salt thereof. The analgesic agent may also be a calcium channel alpha-two-delta ($\alpha_2\delta$) ligand such as pregabalin or gabapentin, or a voltage-gated sodium channel (VGSC) blocker such as lidocaine, lorcainide, mepivacaine hydrochloride, mexiletine hydrochloride, orphenadrine citrate, ambroxol hydrochloride, carbamazepine, ceratotoxin-2, ralfinamide mesylate, tetrodotoxin, or tolperisone hydrochloride. The analgesic agent can be from about 0.001 to about 0.5 wt. % of the topical composition.

The topical composition can include additional ingredients such as other carriers, moisturizers, oils, fats, waxes, surfactants, thickening agents, antioxidants, viscosity stabilizers, buffers, preservatives, perfumes, dyestuffs, humectants, emollients, dispersants, sunscreens, antibacterials, antifungals, disinfectants, vitamins, or antibiotics, as well as other materials that do not have an adverse effect on the activity of the topical composition. The selection of topical excipients is well within the skill of the art, and especially with reference to one of the many standard texts in the art, such as Remington's Pharmaceutical Sciences, 17th Edition, Mack Publishing Company, Easton, Pa., USA (updated in Gennaro, A. R. (Ed.), Remington: The Science and Practice of Pharmacy, $20^{th}$ edition, Lippincott, Williams & Wilkins). For example, the topical composition can comprise from about 0.001 to about 10 wt. % of at least one vitamin, fatty acid, antioxidant, anti-inflammatory agent, antifungal agent, antimicrobial agent, moisturizing agent, emollient, exfoliant, or carbamide.

Prescribing physicians can also include prescription drugs such as amitriptyline, pregabalin, or clonidine to the topical composition at their own discretion when the composition is compounded by a pharmacy. In these instances, the topical composition acts as a nutraceutical base for the drug. A physician may include such drugs during initial treatment with the topical composition and remove them from the prescribed topical composition as symptomology improves, but continue treatment with the topical composition to maintain treatment of the peripheral neuropathy.

Optionally, penetration enhancers can be included in the compositions to facilitate passage of the active ingredients across the skin keratin barrier and into the epidermis. For a discussion of the use of penetration enhancers in topical formulations see generally, Percutaneous Penetration Enhancers (Eric W. Smith & Howard I. Maibach eds. 1995); Ghosh, T. K. et al. 17 Pharm. Tech. 72 (1993); Ghosh, T. K. et al. 17 Pharm. Tech. 62 (1993); Ghosh, T. K. et al. 17 Pharm. Tech. 68 (1993), all of which citations are hereby incorporated herein by reference. The penetration enhancer should be pharmacologically inert, non-toxic, and non-allergenic, have rapid and reversible onset of action, and be compatible with the topical composition. Examples of penetration enhancers include, but are not limited to, dimethyl sulfoxide (DMSO).

Any dermatologically acceptable carrier can be included in the topical compositions, such as topical carriers used in the pharmaceutical compounding arts. The dermatologically acceptable carrier for the topical composition can aid in the percutaneous delivery of the active agents. Such carriers can include liposomes, esters, fatty acids, amides, alcohols, polyols, oils, sulfoxides, water, and combinations thereof. Exemplary carriers are Lipoderm® and Vanpen®, both commercially available from Professional Compounding Centers of America, Houston, Tex. Typically, the carrier is more than 70 wt. % of the total composition.

The topical composition can be formulated as a liquid, solid, semi-solid, or gas. These formulations include without limitation, a cream, lotion, serum, oil, ointment, gel, paste, liniment, powder, spray, aerosol, roll-on liquid, or foam. Additionally, the topical composition can be impregnated into or used as a coating on a bandage, patch, adhesive material, support wrap, glove, sock, footwear, fabric, or similar article for ease of application. Preferably, the topical composition is a cream.

Any topical moisturizer can be applied. Preferably, the moisturizer comprises at least one of the following ingredients: aloe vera extract, green tea extract, *ginseng* extract, jojoba oil, an A vitamer, a D2 vitamer, an E vitamer, oleic acid, or mineral oil. More preferably, the moisturizer contains several of these ingredients or all of these ingredients. The moisturizer can have a pH of about 5.5 to about 6.5. An exemplary moisturizer is Moisturizing Crème™, commercially available from Dr. Lindsey Barth, DPM, of St. Louis, Mo. or from his company Walk Healthy (www.walkhealthy.com).

The moisturizer can comprise a steroid for adipogenesis or lipogenesis in order to stimulate the formation or expansion of subcutaneous adipose tissue. Preferably, the moisturizer comprises about 0.01 to about 10 wt. % of this steroid. Preferably, the steroid is sarsasapogenin or a plant extract containing sarsasapogenin. Sarsasapogenin is commercially available as the cosmetic ingredient Volufiline® from the Sederma division of Croda International, Edison, N.J.

Exfoliation by chemical means can be done with any exfoliant suitable for use on the skin. Preferably, the exfoliant contains at least one of the following ingredients: aloe vera extract, *ginseng* extract, green tea extract, *angelica* extract, sanchi root extract, *arnica* flower extract, jojoba oil, an A vitamer, an E vitamer, urea, or lactic acid. More preferably, the exfoliant contains several of these ingredients or all of these ingredients. The exfoliating composition can have a pH of about 4.5 to about 5.5. An exemplary exfoliating composition is Exfoliating Lotion™, commercially available from Dr. Lindsey Barth, DPM, of St. Louis, Mo. or from his company Walk Healthy (www.walkhealthy.com).

As used herein, "adipogenesis" (or adipocyte differentiation) is a process of cell differentiation by which preadipocytes become adipocytes.

As used herein, "lipogenesis" is a process that encompasses both the processes of fatty acid synthesis and subsequent triglyceride synthesis, when fatty acids are esterified with glycerol to form fats.

As used herein, "subcutaneous adipose tissue" or hypodermis, is the innermost layer of skin. The subcutaneous adipose tissue is constituted by adipocytes.

The term "treating" or "treatment" as used herein includes achieving a therapeutic benefit. By therapeutic benefit is meant eradication, amelioration, or prevention of the underlying disorder being treated. For example, in a diabetes patient, therapeutic benefit includes eradication or amelioration of the underlying diabetic peripheral neuropathy. In some treatment regimens, the topical composition of the invention may be administered to a patient at risk of developing peripheral neuropathy or to a patient reporting one or more of the physiological symptoms of peripheral neuropathy, even though a diagnosis of peripheral neuropathy may not have been made. For example, the topical composition may be applied to a diabetes mellitus patient who has not had symptomology of diabetic peripheral neuropathy. Such a patient would be at risk for developing a peripheral neuropathy.

A "vitamer," as used herein, refers to any compound that has any biological activity in any biological assay for the corresponding vitamin of the same name. A vitamer includes any prodrug of the corresponding vitamin.

Having described the invention in detail, it will be apparent that modifications and variations are possible without departing from the scope of the invention defined in the appended claims.

EXAMPLES

The following non-limiting examples are provided to further illustrate the present invention.

Example 1: Composition

Exemplary compositions according to the invention comprise:

| Topical Cream 1A: | |
|---|---|
| Benfotiamine | 15.0 wt. % |
| Pyridoxal-5'-phosphate | 3.5 wt. % |
| 5-MTHF $Ca^{2+}$ | 0.3 wt. % |
| Morphine | 0.05 wt. % |
| Vanpen ® | 81.15 wt. % |
| Topical Cream 1B: | |
| Benfotiamine | 15.0 wt. % |
| Pyridoxal-5'-phosphate | 3.5 wt. % |
| 5-MTHF $Ca^{2+}$ | 0.3 wt. % |
| Vanpen ® | 81.2 wt. % |

The compositions are prepared by mixing the active ingredients with the carrier. The order of addition of the ingredients is not critical.

Example 2: Treatment of Subject with Diabetic Peripheral Neuropathy

Men and women having diabetic peripheral neuropathy were screened to assess the appearance of the skin and elasticity, peripheral appendage strength and flexibility, gait, ankle reflexes, and any presence of ulceration, and Semmes Weinstein filament testing was performed. In some cases, electromyography, ultrasound therapy and/or blood testing was also performed prior to initiation of the study. Symptomology generally included pain, numbness and/or tingling. Many of the subjects had previously been treated with Cymbalta®, Lyrica® or Nucynta® and were either unresponsive or suffered adverse side effects that prevented continued treatment. A skin punch biopsy was obtained from an ankle of each subject as a control using standard procedures.

Subjects were instructed to apply topical cream 1B of example 1 to their feet once each morning, and to apply Moisturizing Crème™ (Dr. Lindsey Barth, DPM, of St. Louis, Mo.) within 20 to 30 minutes after applying topical cream 1B. Depending upon the severity of the patient's DPN, some patients were instructed to apply topical cream 1B within one hour of the first application of topical cream 1B. Subjects were also instructed to apply topical cream 1B to their feet in the evening, and to apply Exfoliating Lotion™ (Dr. Lindsey Barth, DPM, of St. Louis, Mo.) one hour after application of the topical cream 1B. In some cases where a subject had excessively dry skin with cracking, the subject was instructed to mechanically exfoliate prior to application of Exfoliating Lotion™.

After one or two weeks of treatment, symptomatic relief was achieved in most subjects. Some subjects with more severe symptomology required more weeks of treatment before achieving symptomatic relief. A 3 mm skin punch biopsy is obtained within three to six months of treatment depending upon the subject's response. The control biopsy and the post-treatment biopsy are analyzed to determine epidermal nerve fiber density, and compared to determine the effectiveness of treatment.

Example 3: Treatment of Subject with Peripheral Neuropathy

Men and women having peripheral neuropathy may be screened to assess the appearance of the skin and elasticity, peripheral appendage strength and flexibility, gait, ankle reflexes, and any presence of ulceration, and Semmes Weinstein filament testing may be performed. In some cases, electromyography, ultrasound therapy and/or blood testing is performed prior to initiation of the study. Symptomology will depend upon the type of peripheral neuropathy being treated, but will typically include pain, numbness and/or tingling. A 3 mm skin punch biopsy is obtained from each subject as a control using standard procedures.

Subjects are instructed to apply topical cream 1B of example 1 to their peripheral appendages once each morning, and to apply Moisturizing Crème™ (Dr. Lindsey Barth, DPM, of St. Louis, Mo.) within 20 to 30 minutes after applying topical cream 1B. Depending upon the severity of the patient's DPN, some patients are instructed to apply topical cream 1B within one hour of the first application of topical cream 1B. Subjects are also instructed to apply topical cream 1B to their appendages in the evening, and to apply Exfoliating Lotion™ (Dr. Lindsey Barth, DPM, of St. Louis, Mo.) one hour after application of the topical cream 1B. In some cases where a subject has excessively dry skin with cracking, the subject is instructed to mechanically exfoliate prior to application of Exfoliating Lotion™.

Symptomatic relief is expected to be achieved in most subjects within one to several weeks of initiating treatment. A 3 mm skin punch biopsy is obtained within three to six months of treatment depending upon the subject's response. The control biopsy and the post-treatment biopsy are analyzed to determine epidermal nerve fiber density, and compared to determine the effectiveness of treatment.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description shall be interpreted as illustrative and not in a limiting sense.

What is claimed is:

1. A method for the treatment of diabetic peripheral neuropathy comprising applying to a peripheral appendage of a subject in need of such treatment a topical composition for at least three months to treat the peripheral neuropathy, the topical composition comprising about 5.0 to 25.0 wt. % of a B1 vitamer, about 0.1 to 15.0 wt. % of a B6 vitamer, and about 0.01 to 5.0 wt. % of a B9 vitamer in a dermatologically acceptable carrier, the dermatologically acceptable carrier and any other ingredients other than the B1, B6 and B9 vitamers comprising at least 60 wt. % of the topical composition wherein treatment of diabetic peripheral neuropathy comprises an increase in epidermal nerve fiber density after three months of treatment as compared to the epidermal nerve fiber density of the subject when treatment is initiated.

2. The method of claim 1 wherein the topical composition further comprises about 0.001 to 0.5 wt. % of an opioid analgesic agent.

3. The method of claim 2 wherein the opioid analgesic agent comprises morphine, hydromorphone, oxycodone, hydrocodone, oxymorphone codeine, tramadol, tapentadol, buprenorphine, norbuprenorphine, fentanyl, levorphanol, methadone, loperamide, or a salt thereof.

4. The method of claim 1 wherein the B1 vitamer comprises thiamine, thiamine monophosphate, thiamine pyrophosphate, thiamine triphosphate, benfotiamine, or a salt thereof.

5. The method of claim 1 wherein the B6 vitamer comprises pyridoxine, pyridoxal, pyridoxamine, pyridoxine-5'-phosphate, pyridoxal-5'-phosphate, pyridoxamine-5'-phosphate, or a salt thereof.

6. The method of claim 1 wherein the B9 vitamer comprises folic acid, dihydrofolate, tetrahydrofolate, 5,10-methylenetetrahydrofolate, 5-formiminotetrahydofolate, 5-formyltetrahydrofolate, 5-methyltetrahydrofolate, or a salt thereof.

7. The method of claim 1 wherein the topical composition comprises benfotiamine, pyridoxal-5'-phosphate, and calcium 5-methyltetrahydrofolate.

8. The method of claim 1 wherein the topical composition further comprises about 0.001 to 0.5 wt. % of a calcium channel alpha-two-delta ($\alpha_2\delta$) ligand.

9. The method of claim 8 wherein the calcium channel alpha-two-delta ($\alpha_2\delta$) ligand comprises pregabalin or gabapentin.

10. The method of claim 1 wherein the topical composition further comprises about 0.001 to 0.05 wt. % of a voltage-gated sodium channel (VGSC) blocker.

11. The method of claim 10 wherein the voltage-gated sodium channel (VGSC) blocker comprises lidocaine, lorcainide, mepivacaine hydrochloride, mexiletine hydrochloride, orphenadrine citrate, ambroxol hydrochloride, carbamazepine, ceratotoxin-2, ralfinamide mesylate, tetrodotoxin, or tolperisone hydrochloride.

12. The method of claim 1 wherein the topical composition comprises from about 0.001 to 10 wt. % of at least one vitamin, fatty acid, antioxidant, anti-inflammatory agent, antifungal agent, antimicrobial agent, moisturizing agent, emollient, exfoliant, or carbamide.

13. The method of claim 1 wherein the dermatologically acceptable carrier comprises an ointment base, the dermatologically acceptable carrier being at least 70 wt. % of the topical composition.

14. The method of claim 1 wherein the topical composition is in the form of a cream, lotion, serum, oil, ointment, gel, paste, liniment, powder, spray, aerosol, roll-on liquid, or foam, or is impregnated into, or used as a coating on, a bandage, patch, adhesive material, dressing, support wrap, glove, sock, footwear, or fabric.

15. The method of claim 1 wherein the topical composition is applied at least twice daily.

16. The method of claim 15 wherein the topical composition is applied three to four times daily for about the first month of use, and is applied twice daily thereafter.

17. The method of claim 1 further comprising applying a topical moisturizer to the appendage at least 20 minutes after application of the topical composition.

18. The method of claim 17 wherein the topical moisturizer or the topical composition further comprises about 0.01 to 10 wt. % of a plant steroid for adipogenesis or lipogenesis.

19. The method of claim 18 wherein the plant steroid comprises sarsasapogenin.

20. The method of claim 17 wherein the topical moisturizer comprises aloe vera extract, green tea extract, *ginseng* extract, jojoba oil, an A vitamer, a D2 vitamer, an E vitamer, oleic acid, or mineral oil and optionally has a pH of about 5.5 to about 6.5.

21. The method of claim 1 further comprising mechanically or chemically exfoliating the appendage at least one hour after application of the topical composition.

22. The method of claim 21 wherein an exfoliating composition is applied to the appendage, the exfoliating composition comprising aloe vera extract, *ginseng* extract, green tea extract, *angelica* extract, sanchi root extract, *arnica* flower extract, jojoba oil, an A vitamer, an E vitamer, urea, or lactic acid, and optionally has a pH of about 4.5 to about 5.5.

23. The method of claim 17 further comprising an additional application of the topical composition to the appendage at least one hour after initial application of the topical composition.

24. The method of claim 1 wherein the subject is a human.

25. The method of claim 1 wherein the appendage comprises a hand, a foot, or a limb stump.

26. The method of claim 1 wherein the method further comprises obtaining a skin biopsy sample from the appendage both before and after a period of treatment with the topical composition; determining an amount of at least one nucleic acid or protein in the sample, wherein the nucleic acid or protein is a surrogate marker of diabetic peripheral neuropathy and the change in the amount of the nucleic acid or protein present after the treatment period as compared to the amount present before treatment can indicate the subject's compliance with the treatment protocol.

27. The method of claim 26 wherein the skin biopsy sample is a skin punch biopsy sample.

28. The method of claim 26 wherein compliance is determined after the subject indicates that symptomology of diabetic peripheral neuropathy has been alleviated.

29. A method for the treatment of diabetic peripheral neuropathy comprising applying to a peripheral appendage of a subject in need of such treatment a topical composition for at least six months to treat the peripheral neuropathy, the topical composition comprising about 5.0 to 25.0 wt. % of a B1 vitamer, about 0.1 to 15.0 wt. % of a B6 vitamer, and about 0.01 to 5.0 wt. % of a B9 vitamer in a dermatologically acceptable carrier, the dermatologically acceptable carrier and any other ingredients other than the B1, B6 and B9 vitamers comprising at least 60 wt. % of the topical composition, wherein treatment of diabetic peripheral neuropathy comprises an increase in epidermal nerve fiber density after six months of treatment as compared to the epidermal nerve fiber density of the subject when treatment is initiated.

* * * * *